(12) United States Patent
Perkins

(10) Patent No.: US 8,853,636 B2
(45) Date of Patent: Oct. 7, 2014

(54) LINEAR ACCELERATORS

(75) Inventor: Clifford William Perkins, Crawley (GB)

(73) Assignee: Elekta AB (Publ), Stockholm (SE)

( * ) Notice: Subject to any disclaimer, the term of this patent is extended or adjusted under 35 U.S.C. 154(b) by 463 days.

(21) Appl. No.: 13/407,996

(22) Filed: Feb. 29, 2012

(65) Prior Publication Data

US 2013/0221243 A1    Aug. 29, 2013

(51) Int. Cl.
*G21K 1/02*       (2006.01)
*A61N 5/10*       (2006.01)
*G01N 23/02*      (2006.01)

(52) U.S. Cl.
USPC ............ 250/363.1; 250/427; 250/474.1; 250/492.3; 250/482.1; 378/20; 378/21; 378/29; 378/62; 378/65; 378/147; 378/148; 378/150

(58) Field of Classification Search
USPC ......... 250/358.1, 363.01, 363.05, 363.1, 250/370.08, 370.09, 370.1, 427, 472.1, 250/473.1, 474.1, 482.1, 491.1, 492.1, 250/492.3; 378/1, 4, 6, 7, 10, 20, 21, 22, 378/29, 55, 62, 64, 65, 70, 86, 87, 89, 90, 378/145, 147, 148, 150, 156–159
See application file for complete search history.

(56) References Cited

U.S. PATENT DOCUMENTS

| | | | | |
|---|---|---|---|---|
| 4,198,570 A | | 4/1980 | McHugh et al. | 250/503 |
| 4,549,307 A | * | 10/1985 | Macovski | 378/145 |
| 4,727,562 A | * | 2/1988 | Belanger | 378/98.4 |
| 7,486,773 B2 | * | 2/2009 | Maltz et al. | 378/90 |
| 7,801,271 B2 | * | 9/2010 | Gertner et al. | 378/65 |
| 8,494,116 B2 | * | 7/2013 | Gertner et al. | 378/65 |
| 2004/0096033 A1 | * | 5/2004 | Seppi et al. | 378/65 |
| 2008/0067386 A1 | * | 3/2008 | Maltz et al. | 250/311 |
| 2011/0075815 A1 | | 3/2011 | Brown et al. | 378/125 |
| 2012/0294424 A1 | * | 11/2012 | Chin et al. | 378/65 |
| 2014/0037063 A1 | * | 2/2014 | Gertner et al. | 378/65 |

FOREIGN PATENT DOCUMENTS

| | | | | |
|---|---|---|---|---|
| RU | 2008/138418 | 4/2010 | | G21K 5/04 |
| WO | WO 2005/023366 A1 | 3/2005 | | A61N 5/10 |
| WO | 2009/138753 | 11/2009 | | A61N 5/10 |

OTHER PUBLICATIONS

European Patent Office, Extended European Search Report, 13155306.7—1652, date of mailing May 7, 2013, 6 pages.

* cited by examiner

*Primary Examiner* — Bernard E Souw
(74) *Attorney, Agent, or Firm* — Sunstein Kann Murphy & Timbers LLP

(57) ABSTRACT

The primary collimator for a radiotherapy apparatus can be made up of several layers, each comprising several apertures, and each layer being moveable so as to select a specific aperture to build up the primary collimator shape. In this way, the shape of the primary collimator can be tailored and/or the beam filters incorporated into the primary collimator assembly. This saves space in the radiation head whilst also allowing filters to be easily interchanged.

9 Claims, 3 Drawing Sheets

LINEAR ACCELERATORS

FIELD OF THE INVENTION

The present invention relates to linear accelerators, especially (but not exclusively) those for use in medical applications such as radiotherapy.

BACKGROUND ART

A linear accelerator ("linac") generally consists of an electron gun that accelerates electrons to relativistic speeds, an optional target onto which the electron beam is directed in order to produce an x-ray beam, and guidance apparatus to shape and direct the resulting electron or x-ray beam as required.

The guidance apparatus for a linear accelerator intended for medical use generally comprises a primary collimator, to limit the beam into a generally conical shape, one or more of a range of filters to adjust the energies present in the beam and/or to adjust the distribution of those energies, and various secondary collimators such as block collimators and multi-leaf collimators. The primary collimator and any filters aim to create a uniform generic wide-aperture x-ray or electron beam, which is then shaped as required for a specific treatment by the secondary collimation.

The filters that are available for use in such apparatus usually include sections of solid material (such as Nickel) which have an x-ray absorption spectrum corresponding to an energy which needs to be removed from the x-ray beam, flattening filters which have a varying thickness (or other property) across the field of the beam so as to alleviate irregularities in the beam intensity across that field, and (for electron beams) filters having a material and a thickness able to condition the beam and/or preserve the vacuum within the linear accelerator.

At present, such beam modification filters have to be positioned between the primary collimator wheel and the secondary collimation device. They are usually placed in or on a rotating carousel, which is permitted to rotate freely in a manner that does not interfere with the collimator structure. The filters will however produce scattered X-radiation (as will any object placed in the beam), so further shielding needs to be put in place around the filters to prevent unwanted leakage radiation escaping from the head. This in turn increases the mass of the head and hence the mechanical load on the head support arm.

Current linac construction is therefore tailored to the needs of each customer, by placing into each linac machine during construction the combination of filters and beam modifiers that are needed in order to allow the beam energy options that the customer has chosen.

U.S. Pat. No. 4,198,570 discloses a system in which the electron target and beam modification components are contained within a primary collimator. The source, collimator and filter all remain in the same unitary assembly, and there seems to be no ability to interchange different filters.

U.S. Pat. No. 2011/0075815 discloses a system where the beam filters for a radiotherapeutic device are on a wheel that can rotate through an electron beam. The rotating plate can also be translated along an axis to allow the positioning of a light field generator for beam verification.

WO2009/138753 discloses a linear accelerator able to provide both a therapeutic (MV) radiation beam and an investigative (kV) radiation beam. A pair of primary collimators are provided, on a common sliding substrate so that one or the other can be located in the path of the electron beam produced by the accelerator. Each has an associated target, so that one produces MV x-radiation and the other produces bremsstrahlung x-radiation at kV energies. The latter has an associated electron absorber located within the primary collimator. Further interchangeable filters are provided on a carousel after the primary collimator, to condition the x-ray beams for use.

SUMMARY OF THE INVENTION

The present invention therefore provides radiotherapy apparatus comprising a linear accelerator for producing a beam of electrons, optionally an x-ray target for producing a beam of ionising radiation from the electron beam, a primary collimator for delimiting the thus-produced beam to a first extent, at least one variable-geometry collimator for delimiting the beam to a second and lesser extent, wherein the primary collimator consists of a plurality of layers arranged transversely to the beam, each layer having a plurality of apertures and being independently movable so as to bring a selected one of the apertures into the path of the beam, thereby to define a complete collimator shape made up of an aperture from each layer.

The x-ray target can be permanently present so that the thus-produced beam is always an x-ray beam, or it can be omitted completely such that the thus-produced beam is always an electron beam, or is can be present within the machine and movable so as to allow the thus-produced beam to be an electron beam or an x-ray beam according to the choice made by the operator. In the latter circumstance, the x-ray target can be movable between a position in which it is located in the electron beam so as to substantially absorb the electron beam and produce an x-ray beam, and a location in which it is located substantially outside the electron beam.

The layers making up the plurality of layers can be movable by rotation, or by translation. It will usually be easier if either all layers are movable exclusively by rotation, or all layers are movable exclusively by translation, but an arrangement in which some are movable by rotation and some are movable by translation can be envisaged.

One or more filters for the beam can be placed within the apertures. In this way, a filter can be moved into or out of the beam easily by appropriate selection or de-selection of that aperture that contains it. Ideally, several of the apertures contain a filter; these may be in the same layer (so as to allow a choice of filters) or in different layers (so as to allow filters to be combined). The filters can be of a different nature, such as to allow the desired effect to be produced or to cater for the different types of beam (electron or x-ray).

BRIEF DESCRIPTION OF THE DRAWINGS

An embodiment of the present invention will now be described by way of example, with reference to the accompanying figures in which.

DETAILED DESCRIPTION OF THE EMBODIMENTS

Figure 1:
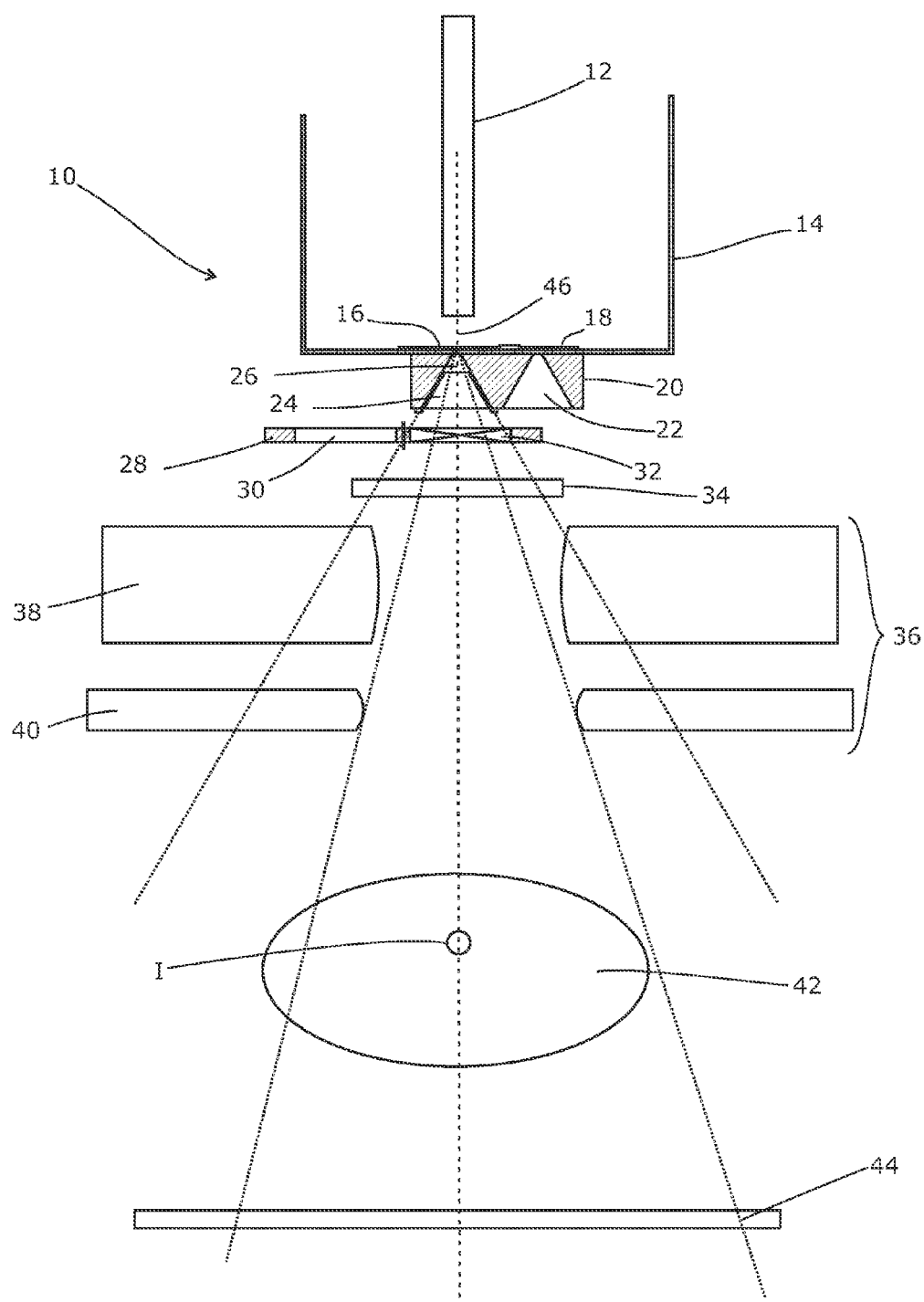
FIG. 1 illustrates the general layout of a typical known form of linear accelerator

FIG. 1 shows the linear accelerator 10 of WO2009/138753. An electron gun 12 (illustrated schematically) such as a linear accelerator is enclosed within a vacuum chamber having an external wall 14. This wall 14 has an aperture 16 which is covered by a sliding carrier 18 that includes a Tungsten/Copper layered x-ray target and an electron window. In one position, the carrier 18 is moved so that the target covers the aperture 16. In another position, the carrier 18 is moved so that the electron window covers the aperture. Thus, in either position the vacuum chamber 14 remains sealed, but the electron beam 46 produced by the electron gun 12 will either pass through the electron window, or will interact with the x-ray target to produce an x-ray beam and be absorbed in the process. In this way, a choice of an x-ray or an electron beam is available for therapeutic use.

The present invention could of course be applied to a device having either an x-ray target only (and hence being unable to produce an electron beam) or an electron window only (and hence being unable to produce an x-ray beam). However, most commercial radiotherapy devices are capable of both these beam types.

Immediately outside the chamber 14 is a primary collimator set 20. This set 20 includes a first primary collimator 22 and a second primary collimator 24 into which has been inserted a carbon absorber 26 held in place with Aluminium support struts. The set 20 is indexable between two positions, akin to the sliding carrier 18, so that one primary collimator of the two is presented in front of the aperture 16.

Beneath the primary collimator set 20, there is a motorised filter carousel 28. This is mounted on an axle offset to one side beneath the aperture 16 and includes a plurality of filter recesses. A first filter recess 30 is (in this case) empty although is could alternatively contain a conventional flattening filter. A second filter recess contains a so-called "bow-tie" filter 32. Bowtie filters are used in CT (computed tomography) scanning for a variety of reasons, including to equalise the signal to noise ratio and to eliminate certain image artifacts etc. Generally, a bow-tie filter is used to compensate the X-ray attenuation for the different thickness regions in the patient, so that uniform X-ray intensity is produced at the detector. It allows a greater intensity to pass in a central region of the beam, progressively attenuating the beam more towards the outer edges.

Below the bow-tie filter 32, there is an ion chamber 34 and a set of collimators generally indicated as 36. This can include elements such as multi-leaf collimators 38, block collimators 40, and the like, operating in one or more planes transverse to the beam.

Below the collimators there will usually be a patient 42 supported on a patient table. Below the patient table is a flat panel scintillator detector 44 (as described above), mounted on an automated imager arm (not shown) which can extend the flat panel detector 44 into place or withdraw it, as required.

Generally, the entire radiation head is mounted so as to be rotatable around a horizontal axis I, taking the flat panel detector 44 with it. The patient 42 is supported on the patient table so that the axis is within the patient. The intersection of the axis with the centre of the beam produced by the radiation head is usually referred to as the "isocentre". It is usual for the patient table to be motorised so that the patient 42 can be positioned as required with the tumour site at or close to the isocentre.

Most radiation heads in use are simpler than that described above, and include (for example) the alternative primary collimators, one with an electron window and one without, according to whether the radiation head is in an x-ray production mode or an electron beam production mode. Typically, all include the carousel 28 for inserting one or more filters into the beam such as a bow-tie or a flattening filter.

Figure 2:
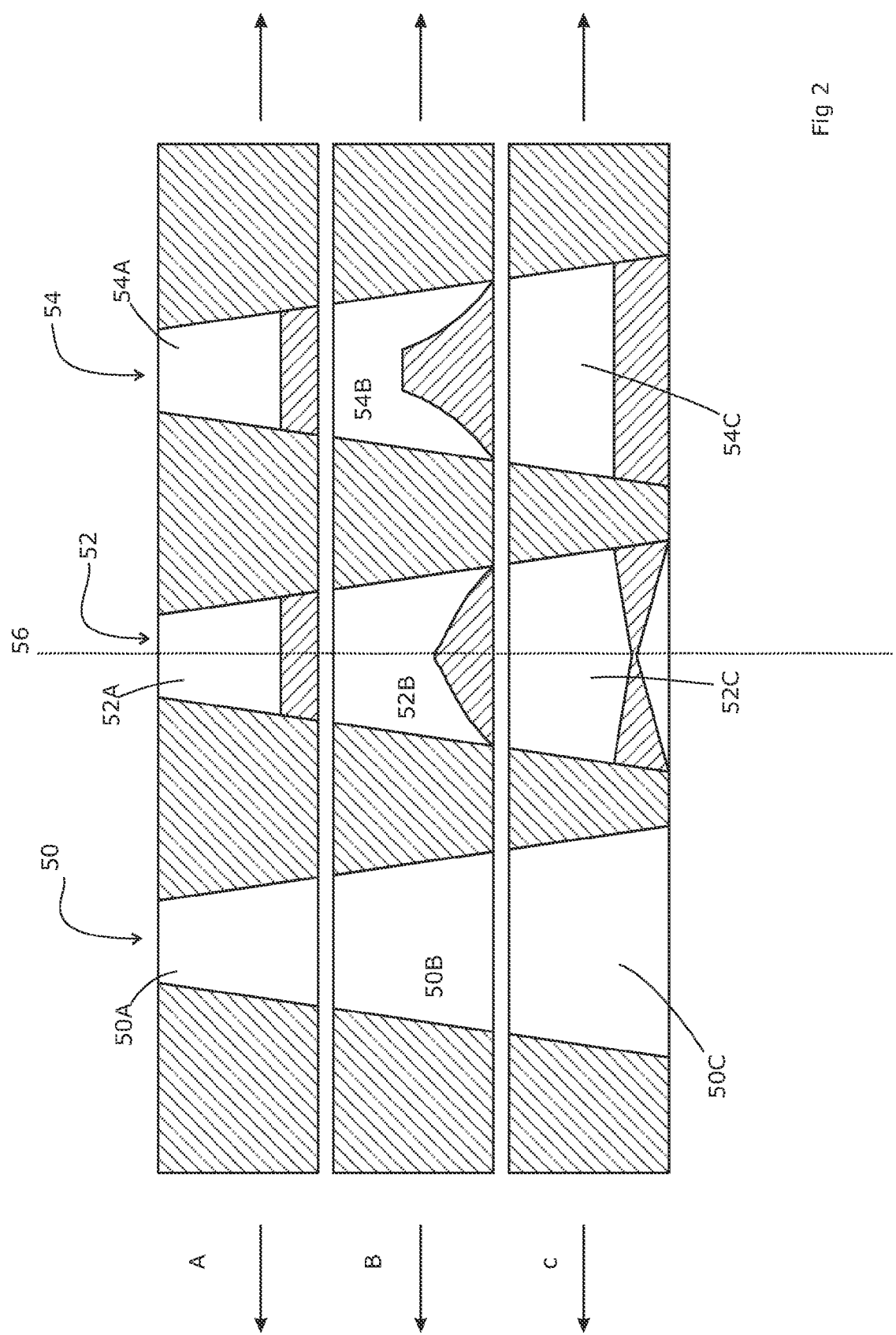
FIG. 2 illustrates a primary collimator according to the present invention.

The idea of the present invention, as illustrated in FIG. 2, is to create a "mix and match" beam modification device which contains multiple elements necessary for both collimation and energy modification, within the same structure. To achieve this, a primary collimator is provided which is split into at least two different sections (in this case, three), each of which is mounted onto a wheel (see FIGS. 3 to 6) or alternative means for moving the sections, such as sliding layers (FIG. 2), so that several alternative collimation sections can be moved into the path of the beam. In this way it is easier to switch between a greater number of different beam configurations compared with the existing system.

Thus, FIG. 2 illustrates schematically the essential parts of a primary collimator according to the present invention, to replace the primary collimator set 20 and optionally the motorised filter carousel 28 of FIG. 1. An upper sliding section A, an middle sliding section B, and a lower sliding section C are all provided on appropriate mounts (not shown), and are able to slide laterally relative to each other and independently of each other. Each sliding section has (in this case) three collimating apertures 50, 52, 54 which are shaped as truncated conical sections, sized so that, together, a collimating aperture from each of the upper, middle and lower sliding sections collectively define a collimator shape that is the desired shape of a primary collimator.

Thus, the upper sliding section A has three apertures 50A, 52A and 54A, the middle sliding section B has three apertures 50B, 52B and 54B, and the lower sliding section C has three apertures 50C, 52C and 54C. As illustrated, the apertures 52A, 52B and 52C are in line with a beam path 56, but the sliding sections can be adjusted so as to collimate the beam 56 using any one of the three upper apertures 50A, 52A and 54A, plus any one of the three middle apertures 50B, 52B and 54B, and any one of the three lower apertures 50C, 52C and 54C.

The apertures are all conically-sided, with the sizes increasing progressively from the upper apertures to the lower apertures so that, when aligned, they together define a smooth conical shape that is the familiar circular-section cone, typical of primary collimators. In this example, all the upper apertures are identical in shape, as are all the middle apertures and all the lower apertures, but this is not necessarily so and the sliding sections could include apertures having alternative shapes or alternative surface treatments. Likewise, the three sliding sections all have the same number of apertures, but if it proved necessary then one or more sliding section could be provided with a greater or lesser number than the others.

Thus, the sliding sections are supported so that one collimating aperture from each can be located in the path of a beam to, together, define a primary collimator. Further, the sliding sections can be moved so that a chosen collimating aperture from each sliding section is brought into register with the beam path and contributes toward the primary collimator shape.

Each aperture of each sliding section is also provided with a beam modifying element which may be one of a beam conditioning filter, a flattening filter, a bow-tie filter, no filter at all (i.e. empty), or any other form of beam modifying element. Conditioning filters usually comprise a sufficient thickness of an element that has an x-ray absorption peak at an energy (or frequency) that corresponds to an energy that needs to be removed or attenuated from the beam. Nickel is commonly used for this purpose. Flattening filters seek to attenuate the beam to a greater extent in its centre section and to a lesser extent at its margins, as the "raw" beam produced by the accelerator often has a greater intensity in its centre section. Thus, a flattening filter creates a more even beam whose images are easier to interpret with the human eye. A bow-tie filter does the opposite, creating a beam that is stronger in its centre section where most of the attenuation in the patient takes place, and whose images are thus more susceptible to CT reconstruction. Each sliding section does however have at least one empty aperture (i.e. no filter at all) to allow electron beam therapy or filter-free X-ray therapy to be performed.

In this example, the apertures are filled as follows:

|  | Aperture 50 | Aperture 52 | Aperture 54 |
| --- | --- | --- | --- |
| Upper Section (A) | Empty | Conditioning filter 1 | Conditioning filter 2 |
| Middle Section (B) | Empty | Flattening filter 1 | Flattening filter 2 |
| Lower Section (C) | Empty | Bow-tie filter | Conditioning filter 3 |

Thus, the filters can be provided in a wide range of combinations. For example, conditioning filter 1 plus flattening filter 2 can be provided by moving the sliding sections so as to align apertures 52A, 54B and 50C. Alternatively, conditioning filters 1 and 3 plus flattening filter 2 can be provided by moving the sliding sections so as to align apertures 52A, 54B and 54C. Existing arrangements can often limit the number and/or nature of filters that can be provided in combination, and the present invention overcomes this.

The structure in which these different beam modification elements are contained is inherently designed to contain scattered X-radiation. Such shielding is normally necessary around a primary collimator in any case, so this adds little or no additional weight to the structure. However, the filter carousel 28 is no longer needed and can be omitted in its entirety, together with the shielding previously provided to cater for the scattered X-radiation that it created. Thus, overall the design of the present invention offers a beam collimator/modifier structure with an overall depth and a weight that is less than if the collimator is to be separated from the beam modification filters. The depth of the radiation head in which the beam collimator/modifier structure is contained needs to be accommodated between the gantry arm and the patient, and a lower-profile head is advantageous. A reduction in the weight of the head also improves the mechanical accuracy of the positioning of the head, as the head must be supported at the end of the support arm in the manner of a cantilever.

FIGS. 3 to 6 show that there a number of different ways this type of beam collimation and profile adjustment (i.e. energy make up of the beam or intensity distribution across the beam) can be arranged for spatial efficiency. Variables include width and depth of collimator layers, movement of axis of rotation and the types of filter placed in each layer (apertures shown blank in some cases, simply to illustrate the aperture variations). It should also be noted that the wheels may be made of more than one type of material. For example, a suitable matrix material of necessary structural rigidity could be used for the main body of each layer, with a higher attenuation material sleeve being inserted into the matrix material for the purposes of collimating the X-rays. For electron collimation, this sleeve material can be made even thinner due to the poorer material-penetrating properties of electrons. In this way, cost, weight, and machining time can be reduced. For the rotating layers, a central shaft can be used for those systems where the rotational axis is aligned between layers. Alternatively, bearings or cog teeth around the outside of the wheel can be provided.

Figure 3:
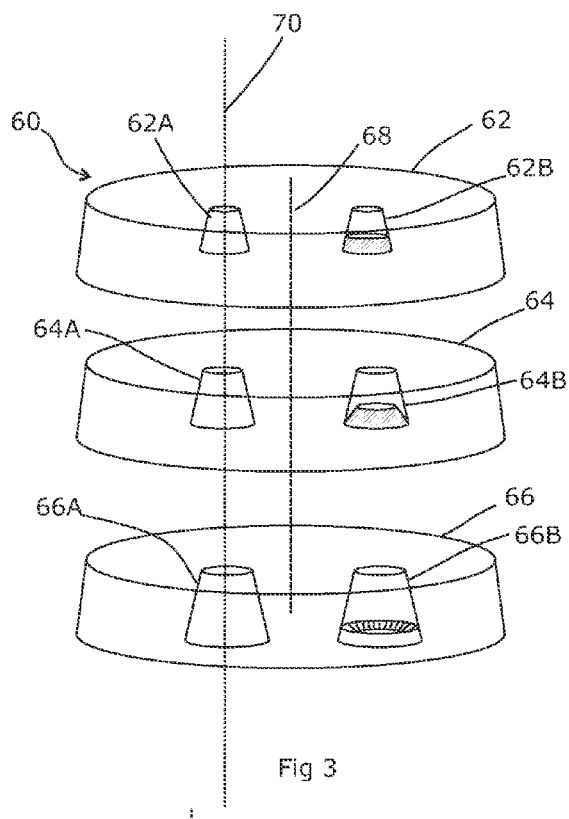
FIGS. 3, 4, 5 and 6 show alternative embodiments of the multi-layer collimator.

Thus, FIG. 3 shows a system 60 with three layers 62, 64, 66, all of the same thickness and all journalled on a common shaft axis 68. Each layer comprises a pair of apertures (A and B), one empty and one containing a filter of various types. Thus, apertures 62A, 64A and 66A are all empty. Aperture 62B contains a Nickel-based beam modifying filter, aperture 64B contains a flattening filter, and aperture 66B contains a bowtie filter. Thus, any combination can be provided of the flattening filter, bowtie filter, or neither, with and without the beam modifying filter, by appropriate rotation of the layers 62, 64, 66 to align the appropriate apertures with the beam path 70 and build up the primary collimator.

Figure 4:
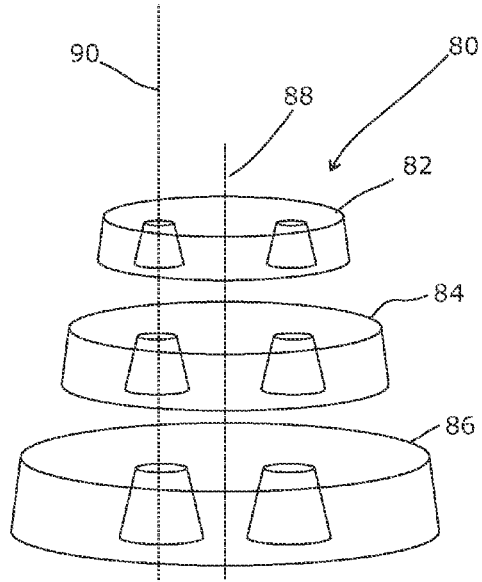

FIG. 4 shows a system 80 in which the width of the layers 82, 84, 86 increases progressively along the beam path 90. The layers all share a common rotation axis 88. The uppermost layer 82 (i.e. that closest to the source) has smaller apertures and the lowest layer 86 has wider apertures, due to the conical nature of the primary collimator shape that needs to be built up. Accordingly, providing the same depth of material around the apertures will mean that the upper layer can be less wide than the lower layer, reducing material usage and weight.

Figure 5:
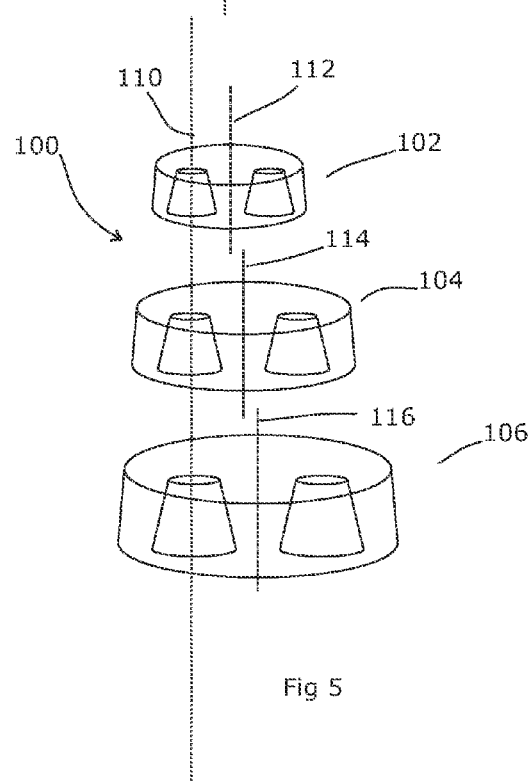

FIG. 5 shows a system 100 in which this is taken one step further. The width of the upper layer 102 is reduced still further, by placing the apertures closer to the rotation axis of that layer. This means that, in order to locate the apertures along the same beam axis 110, each layer needs its own rotation axis. Accordingly, the upper layer 102 rotates about a first axis 112, the middle layer 104 rotates about a second axis 114, and the lower layer 106 rotates about a third axis 116. The axes 112, 114, 166 are spaced progressively further from the beam axis 110 so as to place the progressively larger apertures in alignment as shown.

Figure 6:
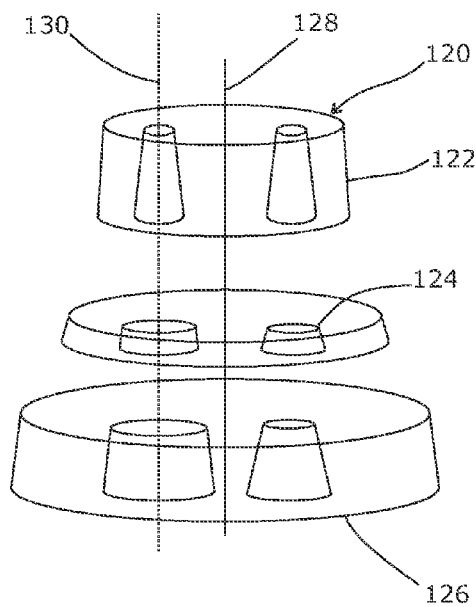

FIG. 6 shows a system 120 in which the three layers 122, 124, 126 have different depths along the beam axis 130, tailored to the depths of the filters that are accommodated within the apertures concerned. These layers are shown with varying widths and journalled on a common rotation axis 128 as in FIG. 4, but they could of course have the same widths as shown in FIG. 3 or individual rotation axes as shown in FIG. 5. Indeed, the variations shown in FIGS. 3 to 6 can be combined as desired.

It will of course be understood that many variations may be made to the above-described embodiment without departing from the scope of the present invention.

The invention claimed is:

1. Radiotherapy apparatus comprising:
   a linear accelerator for producing a beam of electrons,
   optionally, an x-ray target for producing a beam of ionising radiation from the electron beam;
   a primary collimator for delimiting the thus-produced beam to a first extent;
   at least one variable-geometry collimator for delimiting the beam to a second and lesser extent;
   wherein the primary collimator consists of a plurality of layers arranged transversely to the beam, each layer having a plurality of apertures and being independently movable so as to bring a selected one of the apertures into the path of the beam, thereby to define a complete collimator shape made up of an aperture from each layer.

2. Radiotherapy apparatus according to claim 1 in which at least one layer of the plurality of layers is movable by rotation.

3. Radiotherapy apparatus according to claim 1 in which at least one layer of the plurality of layers is movable by translation.

4. Radiotherapy apparatus according to claim 1 in which at least one of the apertures contains a filter for the beam.

5. Radiotherapy apparatus according to claim 1 in which at least two of the layers each include an aperture containing a filter for the beam.

6. Radiotherapy apparatus according to claim 5 in which the filters are different.

7. Radiotherapy apparatus according to claim 1 in which at least one of the layers includes at least two apertures containing a filter for the beam.

8. Radiotherapy apparatus according to claim 7 in which the filters are different.

9. Radiotherapy apparatus according to claim 1 in which the x-ray target is movable between a position in which it is located in the electron beam so as to substantially absorb the electron beam and produce an x-ray beam, and a location in which it is located substantially outside the electron beam.

\* \* \* \* \*